United States Patent
Ghent et al.

[11] Patent Number: 5,910,318
[45] Date of Patent: Jun. 8, 1999

[54] TREATMENT OF IODINE DEFICIENCY DISEASES

[75] Inventors: William R. Ghent, deceased, late of Kingston, Canada, by R. Allison Ghent, executor; Bernard A. Eskin, Philadelphia, Pa.

[73] Assignee: 943038 Ontario Inc., Ontario, Canada

[21] Appl. No.: 08/593,467

[22] Filed: Jan. 29, 1996

Related U.S. Application Data

[63] Continuation-in-part of application No. 08/272,308, Jul. 8, 1994, abandoned, which is a continuation of application No. 07/961,038, Oct. 14, 1992, abandoned, which is a continuation of application No. 07/676,170, Mar. 28, 1991, abandoned, said application No. 08/593,467, is a continuation-in-part of application No. 08/388,026, Feb. 13, 1995, Pat. No. 5,589,198.

[51] Int. Cl.⁶ ..................................................... A61K 33/18
[52] U.S. Cl. ........................ 424/451; 424/464; 424/465; 424/667; 424/668; 424/499; 424/669; 514/899
[58] Field of Search ....................................... 424/451, 667, 424/464, 465, 668, 499, 669; 536/102; 514/899

[56] References Cited

U.S. PATENT DOCUMENTS

| | | |
|---|---|---|
| 59,756 | 11/1866 | Benedict . |
| 1,580,400 | 4/1926 | Bommarito . |
| 2,385,394 | 4/1945 | Witte . |
| 2,816,854 | 12/1957 | Gross . |
| 4,012,504 | 3/1977 | Eckols . |
| 4,564,521 | 1/1986 | Altadonna . |
| 4,744,975 | 5/1988 | Suami et al. . |
| 4,816,255 | 3/1989 | Ghent et al. . |
| 4,886,661 | 12/1989 | Guy et al. . |
| 5,171,582 | 12/1992 | Ghent et al. . |
| 5,250,304 | 10/1993 | Ghent et al. . |
| 5,389,385 | 2/1995 | Ghent et al. . |
| 5,589,198 | 12/1996 | Eskin et al. . |

FOREIGN PATENT DOCUMENTS

| | | |
|---|---|---|
| 1287583 | 8/1991 | Canada . |
| 1336889 | 9/1995 | Canada . |
| 0035882 | 9/1981 | European Pat. Off. . |
| 2318649 | 7/1975 | France . |
| 406964 | 3/1934 | United Kingdom . |
| 668968 | 3/1952 | United Kingdom . |
| 197385 | 7/1967 | United Kingdom . |
| 2079149 | 1/1982 | United Kingdom . |
| 92/17190 | 10/1992 | WIPO . |

*Primary Examiner*—Raj Bawa
*Attorney, Agent, or Firm*—Morrison & Foerster LLP

[57] ABSTRACT

The present invention is concerned with the use of starch containing amylose as a complexant with iodine for preparing dry powder pharmaceutical formulations useful in the preparation of capsules or tablets. The helical structure of the amylose molecule and its ability to complex with smaller molecules including iodine make starch (amylose) a desirable vehicle for the administration of iodine ($I_2$) as a dry powder formulation in capsule or tablet form. These pharmaceutical formulations are particularly useful in the treatment of or the prevention of iodine deficiency diseases including breast dysplasia, breast cancer, endometriosis, premenstrual syndrome, ovarian cysts and radiation sickness from nuclear fallout.

19 Claims, 1 Drawing Sheet

TREATMENT OF IODINE DEFICIENCY DISEASES

CROSS-REFERENCE TO RELATED APPLICATIONS

The present application is a continuation-in-part application of U.S. Ser. No. 08/272,308, filed Jul. 8, 1994, now abandoned, which is a continuation of U.S. Ser. No. 07/961,038 filed Mar. 23, 1993, now abandoned, which is a continuation of U.S. Ser. No. 07/676,170, filed Mar. 28, 1991, now abandoned. This application is also a continuation-in-part application of U.S. Ser. No. 08/388,026, filed Feb. 13, 1995, now issued U.S. Pat. No. 5,589,198. All of the foregoing applications are incorporated herein by reference.

The present invention is concerned with the use of starch containing amylose as a complexant with iodine for preparing dry powder pharmaceutical formulations useful in the preparation of capsules or tablets. More particularly, the invention is concerned with the administration of molecular iodine ($I_2$), in the form of a starch-iodine complex, to patients suffering from iodine deficiency diseases.

BACKGROUND OF THE INVENTION

Heretofore, ($I_2$) has been administered to patients in aqueous molecular form (see related and co-owned U.S. Pat. Nos. 4,816,255; 5,171,582; 5,250,304 and 5,389,385). The administration of aqueous molecular iodine to patients has several disadvantages including the need for specialized dispensers utilizing selective membranes thereby preventing the patient from ingesting crystallized iodine. Standardization of daily dosage is also a problem associated with these dispensers (see U.S. Pat. No. 4,384,960 to Polley).

In view of the apparent disadvantages of the administration of aqueous molecular iodine, it became evident that it would be desirable to administer the iodine in capsule or tablet form. The present invention is directed to dry pharmaceutical formulations containing iodine and the administration of the same in capsule or tablet form. This mode of administering iodine is believed to be superior to those prior art methods and overcomes the various disadvantages experienced by the administration of elemental iodine in aqueous form.

In general, starch contains a mixture of a water-soluble fraction called amylose and a water-insoluble fraction called amylopectin. These two fractions correspond to different carbohydrates of high molecular weight and formula $(C_6H_{10}O_5)_n$. Upon treatment of acid or under the influence of enzymes, the components of starch are hydrolysed progressively to dextrin which is a mixture of low-molecular-weight polysaccharides, (+)-maltose, and finally D-(+)-glucose. Both amylose and amylopectin are made up of D-(+)-glucose units, but differ in molecular size and shape.

Of particular interest is the structure of amylose which is a linear 1,4-acetal polymer of glucose. Thus, amylose is made up of chains of many D-(+)-glucose units, each end joined by an α-glycoside linkage to C-4 of the next glucose unit. It is the alpha linkage at the acetal carbon which has a profound effect on the overall shape of the giant amylose molecule which gives it its unique physical properties and the interactions the amylose molecule may have with smaller molecules.

Amylose is a helical molecule, with glucose residues that coil back on each other, creating a loosely overlapping spiral with a central cavity or tube.

A variety of small molecules including iodine, form weak complexes with amylose. As is known, the starch-iodine complex has a deep blue-violet colour. This colour formation can be used in tests for the presence of either amylose or iodine. From structural evidence, it is apparent that the colour arises because of interactions between rows of $I_3^-$ molecules oriented end to end inside the tubular cavity of amylose structure (see *Organic Chemistry*, Kemp Vellaccio, Worth Publishers, Inc., copyright 1980, p. 994).

It is the unique physical properties of the amylose molecule, which forms a part of starch, which has led us to believe that starch would be ideally suited as a complexant for iodine to prepare dry pharmaceutical formulations which may be encapsulated in capsule or pill form for oral administration. These dry formulations of iodine would be superior to known aqueous iodine solutions used in the treatment or prevention of iodine deficiency diseases such as breast dysplasia, breast cancer, endometriosis, premenstrual syndrome and ovarian cysts. Such aqueous formulations are contemplated in U.S. Pat. No. 4,816,225 to Ghent et al issued Mar. 28, 1989, and WO90/07339, published Jul. 12, 1990. Dry powder formulations of the present invention in capsule or tablet form are also useful in the treatment or prevention of radiation sickness from nuclear fallout and the like and are more easily administrable in oral form to patients. See for example U.S. Pat. No. 4,384,960 to Polley which discloses a dispenser of aqueous elemental iodine for oral administration to prevent or cure iodine-deficient goiter.

SUMMARY OF THE INVENTION

The present invention therefore relates to the preparation of a dry form of elemental iodine ($I_2$) which may be encapsulated in capsule or pill form for therapeutic oral administration to patients in need thereof.

More particularly, the invention relates to the use of starch and more particularly to the use of amylose contained in starch as a complexant with iodine (molecular iodine, $I_2$) to provide means to prepare a dry powder formulation in capsule or tablet form for oral administration to patients suffering from or for prevention of various iodine deficiency diseases and the like.

In one embodiment of the present invention there is provided a method for treating or preventing an iodine deficiency disorder in a human patient comprising administering an effective amount of a starch-iodine complex, wherein the iodine in said complexes is $Ix^-$, wherein x is 3, 5, 7, 9 or 11.

In one further embodiment of the present invention the iodine deficiency disorder is selected from the group consisting of breast-dysplasia, breast cancer, endometriosis, premenstrual syndrome, ovarian cysts and radiation sickness.

According to the present invention the therapeutically effective amount of the starch-iodine complex is that amount that is sufficient to deliver from about 0.01 to about 0.30 milligrams of elemental iodine per kilogram body weight per day.

In a further embodiment of the present invention, the therapeutically effective amount of the starch-iodine complex is that amount that is sufficient to deliver from about 0.03 to about 0.16 milligrams of elemental iodine per kilogram body weight per day.

Further according to the present invention, the therapeutically effective amount of the starch-iodine complex is that amount that is sufficient to deliver from about 1 to about 30 milligrams of elemental iodine per day.

In a further embodiment of the present invention, the therapeutically effective amount of the starch-iodine complex is that amount that is sufficient to deliver from about 2 to about 12 milligrams of elemental iodine per day.

According to a further embodiment of the present invention, the starch in the starch-iodine complex contains from 20% to 100% amylose.

BRIEF DESCRIPTION OF THE DRAWINGS

These and other features of the invention will become more apparent from the following description in which reference is made to the appended drawings wherein.

DESCRIPTION OF PREFERRED EMBODIMENT

Figure 1:
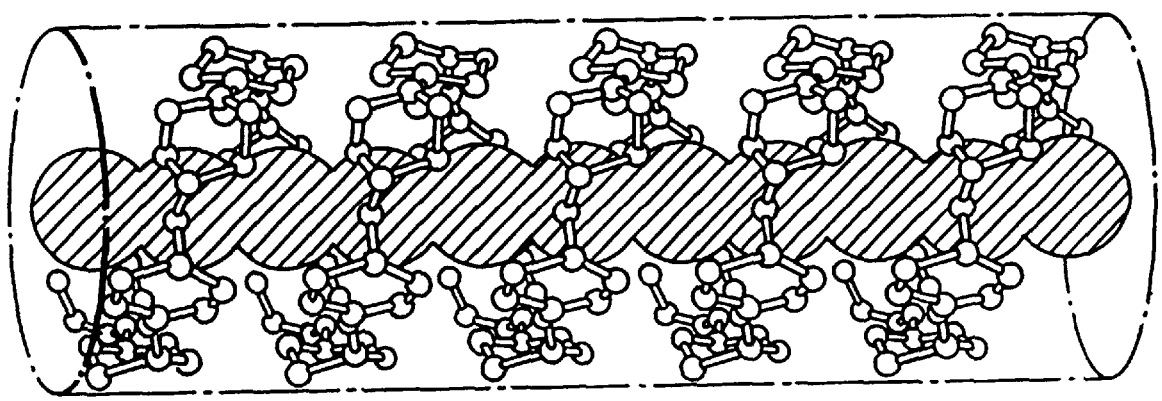
FIG. 1 is a molecular representation of the amylose-iodine complex wherein the iodine molecules depicted as solid spheres fit within the cavity of the amylose helices.

The present invention is concerned with utilizing starch as a complexant with iodine to form an iodine-starch complex. Specifically, this invention is concerned with the use of the amylose component of starch to form an amylose iodine complex as depicted in FIG. 1. (Taken from *Organic Chemistry,* Kemp-Vellaccio, Worth Publishers, Inc. 1980, p. 994.)

It is mostly the linear component of the amylose in starch which is responsible for the uptake of iodine. This starch-iodine complex exists in a helical configuration as depicted in FIG. 1 within which the triiodide ions $I_3^-$) or polyiodide ions ($I_5^-$ up to $I_{11}^-$) reside. The most common complex however is the triiodide ion-amylose complex. The molecular weight or molecular weight distribution of the starch (amylose) plays a critical factor in the ability of starch to complex iodine.

The minimum length of the amylose chain to produce its characteristic blue colour is about 30–40 D-glucose units, providing a cavity corresponding closely in length to an 11-atom polyiodine chain. Therefore, the brand, lot, quality, source, time of harvesting and place of growth are all factors which will influence the linear amylose content of the starches.

In theory, any type of starch, provided that it contains a sufficient amount of amylose to allow a sufficient amount of iodine to complex with the starch, can be used according to the present invention. It will be obvious to persons skilled in the art, that if the content of the amylose is low, and thus, the corresponding amount of iodine complexed in the starch is low, then in order to administer a sufficient amount of iodine for the treatment of iodine deficiency diseases, a larger amount of the complex will have to be administered to the patient. The amount of iodine which can be complexed to various starches has been reported by Larson et al. (*Analytical Chemistry* Vol. 25, 802–804, 1953). It was found that 18.4 grams of iodine complexed with 100 grams of amylose. Using starch with varying amounts of amylose, the amount of iodine, which can complex with the starch will also vary, from 0.149 grams using waxy sorghum to 18.9 grams using corn amylose, both per 100 g of starch.

One example of starch for use in the preparation of the starch-iodine formulation is #7 Hylon starch. This starch is a purified "specialty" starch produced by Nacan Products of Toronto, Ontario, Canada. The starch is made from a hybrid corn called Hylon #7 which contains 70 percent amylose and 30 percent amylopectin. From the use of such a specialty starch containing a high proportion of amylose, the amount of iodine in the complex is now determined from the amount of iodine supplied to the complex rather that the amount of iodine that can be bound by the starch amylose.

A starch containing less than 70% amylose is still within the scope of the present invention. However, in using such a starch, particularly a starch with a very low amylose content, the amount of iodine that can be bound by the starch becomes the determining factor, rather than the amount of iodine which one provides to complex with the starch. It is obvious that from the point of view of controlled dosage, it would be preferable to use a starch which contains a high percentage of amylose, where one could therefore closely and specifically control the amount of iodine in the starch by simply controlling the amount of iodine supplied to the complex.

It is equally obvious that a starch containing greater than 70% amylose is also within the scope of the present invention. In a starch sample containing 70% or more of amylose, the amount of iodine bound to the starch would be a function of the amount of iodine that is supplied to the starch.

Therefore, as previously stated, in theory any starch, with any proportion of amylose, can be used according to the present invention. For example a starch containing from about 20% to about 100% amylose could be used in the present invention. A starch containing 50% to 80% amylose can also be used according to the present invention.

In the preparation of the iodine-starch (amylose) complex, since the iodine will ultimately be used to treat human patients, high quality re-sublimed iodine should be employed in the preparation.

In determining a method for the production of the desired iodine-starch complex, the effect of temperature on the capacity of starch to absorb iodine must be examined. The effective temperature is best described by Hatch (*Analytical Chemistry,* Vol. 54, 2002 (1982). At higher temperature (especially at 60° C.), there is a temperature-dependant change in the structure and (or) number of starch helices available for reaction with iodine (triiodide ions). In fact, the thermal decoloration of the blue starch-iodine complex is the result of thermally induced deterioration or unravelling of the starch helices from around the iodine (triiodide ions ($I_3^-$) or others). This phenomenon is called hysteresis effect and is reversible at least up to 40° C. As discussed by Hatch supra, the complex does not decolorize completely until warmed to 38° C. (±1° C.) which is essentially at body temperature.

As noted above, the complexing of the iodine with starch is primarily in the form of triiodide ions ($I_3^-$). The present invention, however, is primarily concerned with the preparation of a dry formulation of iodine for oral consumption to supply elemental iodine ($I_2$) for treatment of iodine deficiency diseases and the like.

In order to understand how $I_2$ is supplied to the patient, one must understand how iodine, in predominately triiodide form, is released from starch. There are three different methods for releasing the iodine from the starch molecule which include:

a) thermally which induces the unfolding of the amylose helices;

b) by acid hydrolysis of starch down to D-glucose in aqueous solutions; or c) by amylase treatment.

For a detailed description of the last two methods see, for example, Robyt, *Starch, Chemistry and Technology,* p. 94.

It is the latter treatment, i.e. that of amylase which is involved in the in vivo degradation of starch. Specifically, salivary amylase degrades starch (amylose) to maltose (a disaccharide) and to higher oligosaccharides. Very little, if any, hydrolysis of starch takes place in the stomach. After some time in the stomach, the food material passes into the small intestine and is neutralized. Pancreatic α-amylase is secreted into the small intestine from the pancreatic duct and completes the hydrolysis of the starch. To convert the α-amylase products into D-glucose, two other enzymes are required, an α-1→4 glucosidase and an α-1→6 glucosidase. These enzymes are secreted by the brush border cells of the lining of the small intestine and by the pancreas. These enzymes do not have any action on starch per se, but their combined action completes the conversion of starch to D-glucose.

Thus, it can be seen from the foregoing, that once the encapsulated starch-iodine complex is ingested, it is acted upon by the upper small bowel contents including α-amylase, bile and pancreatic enzymes containing amylase and glucosidases. The amylase, aided by bile, will digest the amylose and thereby release the $I_3^-$ from the complex.

$I_3^-$ cannot exist as a molecule (uncomplexed) and immediately breaks down to $I_2$ and $I^-$. The $I^-$ is picked up by the sodium, potassium and proteins of the food stuffs to produce iodides, while the $I_2$ is absorbed as $I_2$ in the same fashion as when $I_2$ is administered in an aqueous vehicle.

The absorption of molecular iodine $I_2$ in aqueous form however, takes place predominantly in the stomach through the gastric mucosa, predominantly in the form of $I_2$. Owing to the difference in pH of the intestine as compared to the stomach, one would have expected that the predominant form of iodine once it had been released from the starch-iodine complex of the present invention would be $I^-$. Accordingly, one would have expected that the starch-iodine formulation would not provide the same clinical results as seen with the use of the aqueous solution of elemental iodine. In the contrary, it would have been expected that the results seen with the starch-iodine complex would be similar to those obtained using potassium iodide. However, as will be demonstrated in the present application, the starch-iodine complex is an effective formulation for the treatment of iodine-deficiency diseases. Effectiveness results from the fact that, despite the teachings of the prior art, $I_2$ is released from the starch-iodine complex. $I_2$ is absorbed directly into the blood stream, which probably shifts the equilibrium to the formation of more $I_2$ than one would have expected in an equilibrium solution.

It can be seen from the foregoing, that the starch-iodine ($I_3^-$) complex is ideally suited to produce a dry formulation for oral administration of iodine due to the immediate conversion of the triiodide ion to $I_2$ in vivo.

The dosage of elemental iodine can also be varied by varying the amount of starch-iodine complex in the final tablet formulation. Thus, it is clear that the relative amounts of the iodine or starch in the complex is not critical. Any starch-iodine complex can be used, provided that it is capable of delivering from about 1 to about 30 milligrams of elemental iodine per day.

It has been found that a daily dose of about 1 milligram to about 30 milligrams of elemental iodine ($I_2$) is effective in the treatment or prevention of iodine deficiency diseases. A daily dosage of 2 to 12 milligrams of elemental iodine has also been found to effective in the treatment or prevention of iodine deficiency diseases. A daily dosage of about 3 milligrams to about 6 milligrams of elemental iodine has further been found to be effective for the treatment or prevention of iodine deficiency diseases. The exact dosage can be selected depending upon the patient's needs, as determined by the practicing physician.

Based on the body weight of the patient, it has been found that a daily dosage of 0.01 to 0.30 milligrams of elemental iodine, per kilogram body weight of the patient is effective for the treatment or prevention of iodine deficiency diseases. It has further been found that a daily dosage of from about 0.03 to about 0.16 milligrams of the elemental iodine per kilogram of body weight of the patient is effective for the treatment or prevention of iodine deficiency diseases. It has further been found that a daily dosage rate of about 0.7 milligrams to about 0.9 milligrams of elemental iodine per kilogram body weight of the patient is also effective for the treatment or prevention of iodine deficiency diseases. In one example of the present invention, the elemental iodine as administered in a starch-iodine complex in tablet form, wherein each tablet contains 3 milligrams of elemental iodine. The patient may be prescribed to take from 1 to 9 tablets a day. In most instances 1 to 3 tablets a day may be required.

In one example of the present invention the complex contains 3 milligrams of iodine, in the form of triiodide or polyiodide ions, in 70 milligrams starch, wherein said starch has a 70% amylose content. Thus, the amount of iodine per amylose is about 3 mg iodine to 49 mg amylose. This complex can be directly encapsulated for use without the use of any fillers.

As stated previously, any ratio of starch and iodine can be used, provided that it is capable of delivering from about 1 to about 30 milligrams of iodine to the patient. For example the starch-iodine complex can contain from about 0.25 mg to about 10 mg of iodine and from about 10 mg to about 300 mg of starch. In a further example, the amount of iodine in the starch-iodine complex is from about 1 mg to about 5 mg and the amount of starch is from about 50 mg to about 100 mg. The precise ratio of starch and iodine can be chosen, depending on the amylose content of the starch, and the iodine to tablet ratio required in the final formulation.

Although the use of additional pharmaceutical adjuvants may not be required, suitable pharmaceutical adjuvants, fillers, excipients etc. may form part of the pharmaceutical composition if desired. For example the complex could be mixed with lactose before forming into a tablet. For convenience the tablet can be made up to a total weight of 300 mg, however, any other convenient weight can also be used.

It is to be understood that the recommended daily dosage of $I_2$ for the treatment of other iodine related diseases such as with the thyroid including radiation sickness etc. may be other than the preferred dosage disclosed hereinabove and thus variation of the amount of aqueous molecular iodine supplied to starch may be increased or decreased depending on the dosage required. Specialty starches such as #7 Hylon starch with its high amylose content are uniquely suited for complexing of an increased amount of iodine and as indicated previously the amount of iodine in the complex is a function of the amount of iodine supplied to the complex rather than the amount of iodine that can be bound by the starch amylose. Other less amylose rich starches may be used, provided there is sufficient amylose present to supply the desired dosage of iodine.

According to the present invention, elemental iodine was admixed with starch to form a starch-iodine complex, wherein the iodine is present as triiodide ions ($I_3^-$) or polyiodide ions ($I_5^-$) up to ($I_{11}^-$). When the starch-iodine complex dissociates elemental iodine $I_2$ is released and is the effective active ingredient of the present invention.

While this invention is described in detail with particular reference to preferred embodiments thereof, said embodiments are offered to illustrate but not limit the invention.

EXAMPLES

Example 1

Preparation of a Starch-Iodine Complex

The starch-iodine complex of the present invention can generally be prepared by the following method. In this example the starch, #7 Hylon is used (70% amylose). This specialized starch is exposed to aqueous molecular iodine (AMI) at room temperature (20° C.) (300 milligrams iodine per liter) in a ratio of 1 gram of starch to 100 milliliters AMI for 12 hours at 20° C.

The iodine solution is prepared by exposing 50 grams of prilled iodine to ion-free water at 20° C. for 4 days.

The chemical reaction of this combination is $$I_2 + H_2O = HOI + I^- + I_2 + I_3^-.$$

The proportion of $I_2$ and $I_3^-$ are temperature dependent as noted above, with an increased temperature increasing the amount of $I_3^-$.

The solution is passed through a microspore filter and is then ready for combination with the starch. The AMI solution combines with the amylose of starch and produces a complex of $I_3^-$ with the amylose helices. The $I_2$ and $I^-$ present in the AMI solution are compressed in the helices to $I_3^-$. It is this combination that produces the colorimetric change to blue.

After exposure of the AMI to starch for 12 hours, the supernatant water is decanted and tested for presence of iodine.

The resulting starch-iodine complex is allowed to dry at room temperature and then mechanically pulverized. It is now ready for encapsulation. In one example the tablets are prepared at a strength of 3 milligrams of iodine in 70 milligrams of the complex. However, as discussed above, the amount of iodine complexed to the starch is a function of the starch which is used, more specifically, the preparation of amylose in the starch which is used and, thus, the 3 milligrams of iodine in 70 milligrams of the complex reflects the specific example when a 70% amylose starch is used to form the complex.

The 70 milligram complex is then admixed with 230 milligrams of lactose to form a 300 milligram tablet containing 3 milligrams of elemental iodine.

Example 2

Treatment of Patients with Iodine Deficiency Diseases with the Starch-Iodine Complex In one study a total of 117 patients were treated with aqueous molecular iodine. From this group 85 were switched to treatment with starch-iodine complex in capsule form, prepared according to Example 1. The treatment extended for a minimum of one month to a maximum of 20 months with a mean treatment time of 8 months. The effects of this treatment were compared to those seen with treatment by aqueous molecular iodine and assessed on the basis of both objective and subjective criteria. The results demonstrated that there were no significant differences between treatments with respect to the positive effects in reversing the manifestations of iodine deficiency. Further, two side effects commonly observed with the aqueous molecular iodine treatment, namely acne and thinning of the hair were not observed in the group receiving the capsules of starch-iodine. Further, no new side effects were noted and patient acceptance was greatly increased.

In a further study, 32 patients not having previously been treated with aqueous molecular iodine were subjected to treatment with starch-iodine in capsule form. This group was treated for a minimum of one month and a maximum of 26 months with a mean of 8.4 months. Observations on this group paralleled those discussed above for the group receiving a similar treatment.

These results demonstrate that starch-iodine administered in capsule form is superior to the aqueous molecular iodine because it not only provides the same positive effects in reversing manifestations of iodine deficiency but does so without unwanted side effects.

In a further study, a starch-iodine complex (3 milligrams of $I_2$ in 70 milligrams starch-70% amylose), prepared as according to Example 1, was administered to about 900 patients with fibrocyctic breast disease. The dosages used in this study ranged from about 0.029 mg/kg body weight to about 0.265 mg/kg body weight. Examples of the dosages administered in this study are depicted in Table 1.

TABLE 1

| Patient No. | Weight (kg) | Milligrams $I_2$/Day | Milligrams $I_2$/kg bw |
| --- | --- | --- | --- |
| 1 | 102.2 | 3 | 0.029354 |
| 2 | 60.2 | 3 | 0.049834 |
| 3 | 117.0 | 6 | 0.051282 |
| 4 | 48.1 | 3 | 0.062370 |
| 5 | 85.3 | 6 | 0.070340 |
| 6 | 75.8 | 6 | 0.079156 |
| 7 | 73.1 | 6 | 0.082079 |
| 8 | 66.3 | 6 | 0.090498 |
| 9 | 56.8 | 6 | 0.105634 |
| 10 | 81.0 | 9 | 0.111111 |
| 11 | 54.4 | 6 | 0.110294 |
| 12 | 42.5 | 6 | 0.141176 |
| 13 | 60.4 | 9 | 0.149007 |
| 14 | 53.5 | 9 | 0.168224 |
| 15 | 68.0 | 18 | 0.264706 |

Since the present invention is subject to many modifications, variations and changes in detail, it is intended that all matters in the foregoing description or shown in the accompanying drawing be interpreted as illustrative and not in a limiting sense.

The embodiments of the invention in which an exclusive property or privilege is claimed are defined as follows:

1. A method for treating an iodine deficiency disorder selected from the group consisting of breast dysplasia, breast cancer, endometriosis, premenstrual syndrome, ovarian cysts and radiation sickness in a patient in need thereof, by orally administering a pill or capsule comprising a therapeutically effective amount of a non-covalent starch-iodine complex to said patient, wherein the starch in the starch-iodine complex contains from 20% to 100% amylose.

2. The method of claim 1, wherein the therapeutically effective amount of the starch-iodine complex is sufficient to deliver from about 0.01 to about 0.30 milligrams of elemental iodine ($I_2$) per kilogram body weight per day.

3. The method of claim 2, wherein the therapeutically effective amount of the starch-iodine complex is sufficient to deliver from about 0.03 to about 0.16 milligrams of elemental iodine ($I_2$) per kilogram body weight per day.

4. The method of claim 1, wherein the therapeutically effective amount of the starch-iodine complex is sufficient to deliver from about 1 to about 30 milligrams of elemental iodine ($I_2$) per day.

5. The method of claim 4, wherein the therapeutically effective amount of the starch-iodine complex is sufficient to deliver from about 2 to about 12 milligrams of elemental iodine (I$_2$) per day.

6. The method of claim 1, wherein the starch in the starch-iodine complex contains from 50% to 80% amylose.

7. The method of claim 6, wherein the starch in the starch-iodine complex contains about 70% amylose.

8. The method of claim 1 wherein the amount of iodine in the starch-iodine complex is from about 0.25 mg to about 10 mg.

9. The method of claim 8 wherein the amount of iodine in the starch-iodine complex is from about 1 mg to about 5 mg.

10. The method of claim 1 wherein the amount of starch in the starch-iodine complex is from about 10 mg to about 300 mg.

11. The method of claim 10 wherein the amount of starch in the starch-iodine complex is from about 50 mg to about 100 mg.

12. A method for treating an iodine deficiency disorder in a patient in need thereof, by administering a therapeutically effective amount of a non-covalent starch-iodine complex to said patient, wherein the starch in said complex contains 70% amylose, is formulated in a ratio of 3 mg of iodine to 70 mg of complex and said therapeutically effective amount is that amount that is sufficient to deliver from about 1 mg to about 30 mg of elemental iodine (I$_2$).

13. The method of claim 5, wherein the therapeutically effective amount of the starch-iodine complex is sufficient to deliver from about 3 to about 6 milligrams of elemental iodine (I$_2$) per day.

14. The method of claim 1, wherein said iodine deficiency disorder is breast dysplasia.

15. The method of claim 1, wherein said iodine deficiency disorder is breast cancer.

16. The method of claim 1, wherein said iodine deficiency disorder is endometriosis.

17. The method of claim 1, wherein said iodine deficiency disorder is premenstrual syndrome.

18. The method of claim 1, wherein said iodine deficiency disorder is ovarian cysts.

19. The method of claim 1, wherein said iodine deficiency disorder is radiation sickness.

* * * * *